(12) United States Patent
Page

(10) Patent No.: US 8,144,021 B2
(45) Date of Patent: Mar. 27, 2012

(54) DEVICE AND APPARATUS FOR DETECTING MOISTURE

(75) Inventor: Anthony Edward Page, Nelson (NZ)

(73) Assignees: Whalley, Robin as Trustee of the Olfarse Trust, Nelson (NZ); Le Gros, Paul Donald as Trustee of the Olfarse Trust, Nelson (NZ)

( * ) Notice: Subject to any disclaimer, the term of this patent is extended or adjusted under 35 U.S.C. 154(b) by 1137 days.

(21) Appl. No.: 11/579,226

(22) PCT Filed: May 12, 2005

(86) PCT No.: PCT/NZ2005/000100
§ 371 (c)(1),
(2), (4) Date: Oct. 31, 2006

(87) PCT Pub. No.: WO2005/107580
PCT Pub. Date: Nov. 17, 2005

(65) Prior Publication Data
US 2008/0246620 A1  Oct. 9, 2008

(30) Foreign Application Priority Data
May 12, 2004 (NZ) ........................................ 532900

(51) Int. Cl.
*G01R 27/02* (2006.01)
(52) U.S. Cl. ........ 340/604; 340/602; 340/603; 340/605; 73/40; 324/512; 324/525
(58) Field of Classification Search .......... 340/602–605; 73/40; 324/512, 525
See application file for complete search history.

(56) References Cited

U.S. PATENT DOCUMENTS

| | | | |
|---|---|---|---|
| 4,191,950 A | | 3/1980 | Levin et al. |
| 4,374,379 A | | 2/1983 | Dennison |
| 4,714,739 A | * | 12/1987 | Arkles ........................ 525/92 G |
| 4,977,906 A | | 12/1990 | Di Scipio |
| 5,291,181 A | | 3/1994 | Deponte |
| 5,381,097 A | * | 1/1995 | Takatori et al. ............... 324/512 |
| 5,449,017 A | * | 9/1995 | Collins et al. ................. 137/312 |
| 5,557,263 A | | 9/1996 | Fisher et al. |
| 6,097,297 A | | 8/2000 | Fard |
| 6,175,310 B1 | * | 1/2001 | Gott ............................. 340/605 |
| 6,480,731 B1 | | 11/2002 | Deluca et al. |
| 2004/0166364 A1 | * | 8/2004 | Kathirgamanathan ........ 428/690 |
| 2004/0170282 A1 | * | 9/2004 | Tahara et al. .................... 381/58 |
| 2005/0195085 A1 | * | 9/2005 | Cretu-Petra ................ 340/573.5 |

FOREIGN PATENT DOCUMENTS

| | | |
|---|---|---|
| DE | 3823859 A1 | 1/1990 |
| GB | 1192421 A | 5/1970 |
| GB | 2272093 A | 5/1994 |
| NZ | 517078 | 8/2003 |
| WO | WO 8100045 A1 | 1/1981 |
| WO | WO 9963497 A1 | 12/1999 |

* cited by examiner

*Primary Examiner* — George Bugg
*Assistant Examiner* — Ojiako Nwugo
(74) *Attorney, Agent, or Firm* — Husch Blackwell LLP

(57) ABSTRACT

A device for detecting the presence of bodily fluid, the device including a detector (1) means having two spaced apart electrodes (2, 3), each electrode is connected to a signal generating means via a lead (6, 7). The electrodes are encased in a flexible non-conductive material with each including at least one protruding conductive element (4). The protruding elements are separated by the same distance as the spacing between the two electrodes. The device also includes a signal processing means that detects a change of state across the electrodes produced by the introduction of a fluid and an alarm actuated by the change of state.

20 Claims, 6 Drawing Sheets

(arrows and circuit diagram continued on sheet 5/6)

(arrows and circuit diagram follow from sheet 4/6)

DEVICE AND APPARATUS FOR DETECTING MOISTURE

TECHNICAL FIELD

This invention relates to a device and apparatus for detecting and monitoring bodily fluids. More particularly, but not exclusively, the invention relates to a device and apparatus for detecting urine and/or blood and/or excessive perspiration and generating an alert signal in response to such detection.

BACKGROUND ART

The early detection of bodily fluids in some situations can be important to the well being of a person. For example, the early detection of any leakage of blood around the site of insertion of a dialysing needle during dialysis treatment, and in particular nocturnal dialysis, may be useful. The detection of other bodily fluids such as perspiration, particularly high levels of perspiration indicating hypoglycaemia in insulin-dependent diabetics, may be important for the wellbeing and care of that person.

Sufferers of enuresis, particularly in relation to nocturnal enuresis causing bedwetting, or diurnal wetting, can be assisted by the use of a detector and alarm unit that serves to wake the person when the presence of urine is detected. A number of disadvantages with many types of devices is that they can be too small to detect the presence of bodily fluid or they can be too large and cause discomfort for the wearer. Many are made from metal, printed circuit board material or other solid and rigid materials that can cause discomfort to the extent of causing significant irritation if they are in contact with the skin of the wearer. Further, some of these detecting devices are typically not durable or robust and need to be replaced after a short period of use.

It is a non-limiting object of the invention to provide a device for detecting bodily fluid which overcomes at least some of the abovementioned problems, or at least to provide the public with a useful choice.

It is a further non-limiting object of the invention to provide an apparatus for detecting bodily fluid and generating an alarm signal which overcomes at least some of the abovementioned problems, or at least to provide the public with a useful choice.

SUMMARY OF THE INVENTION

According to a first aspect of the invention there is provided a device for detecting the presence of bodily fluid, the device including a detector means including at least two spaced apart electrodes defining an open electrical bridge and each electrode being electrically connectable to a signal generating means via a wire, the electrodes being configured and arranged, in use, to provide a path for electricity to conduct across a predetermined distance or gap between the electrodes when a sufficient amount of bodily fluid bridges the distance or gap between the electrodes, and wherein the conductive electrodes are substantially encased in a flexible non-conductive material with each conductive electrode including at least one protruding conductive element separated by the predetermined distance or gap between the electrodes.

Preferably the conductive electrodes are overmoulded with a suitable flexible non-conductive thermoplastics material. Desirably the thermoplastics material is a flexible thermoplastic silicone vulcanizate material. Advantageously each said conductive electrode includes nine protruding conductive elements separated by the predetermined distance or gap between the electrodes.

Preferably the pair of conductive electrodes are configured and arranged with nine protruding conductive elements formed in each said electrode, the conductive elements being exposed through the overmoulded non-conductive thermoplastics material, and wherein the nine opposing conductive elements are aligned along the length of the detector means with the predetermined distance or gap between each opposing pair of conductive elements.

Preferably the wire is adapted to be releasably connectable to the signal processing means.

According to a second aspect of the invention there is provided a moisture detection apparatus including the device of claim 1, and including a signal processing means configured and arranged to detect a change of state across the electrodes and actuate an alarm means, and a power source means for powering the signal processing means and the alarm means.

Preferably the signal processing means and the alarm means are configured and arranged within a housing, and wherein the detector means is located remotely from the housing and connected via the wire to a removably attachable connector means to the input of the signal processing means.

Desirably the signal processing means includes an arrangement of circuit elements configured and arranged, in use, to generate a suitable input signal to an audible alarm means so as to actuate an audible alarm in response to the detection of bodily fluid by the detector means.

Preferably the signal processing means includes an arrangement of circuit elements configured and arranged, in use, to prevent current from flowing through the detecting device once the alarm means is activated. Desirably the alarm is a piezoelectric ceramic speaker.

Alternatively the signal processing means includes a transmitter means that receives a suitable input signal and transmits an output signal to a receiver means, and wherein the receiver means receiving a signal from the transmitter means to actuate an audible alarm means in response to the detection of bodily fluid by the detector means.

Preferably the power source means is a battery supplying a nominal six volt direct current supply.

Optionally the bodily fluid being detected is urine and/or blood and/or excessive perspiration.

BRIEF DESCRIPTION OF THE DRAWINGS

Preferred embodiments of the invention will now be illustrated, by way of example only, with reference to the accompanying drawings in which.

DETAILED DESCRIPTION OF THE DRAWINGS

Referring to FIGS. 1 to 5, a moisture detection device, generally referred to as 1, according to one preferred embodiment of the invention, is illustrated.

The moisture detection device 1 of the invention has been designed to provide increased comfort to users by being substantially flexible and by having properties making it relatively durable and resilient.

In this description references are made to the detection of bodily fluid and/or moisture, and in the case of a bodily fluid it can include urine, blood and/or perspiration/sweat depending on the application of the invention. For ease of reference to these terms the following description will mainly refer to moisture, although it will be appreciated that the device 1 of the invention can detect a variety of bodily fluids.

The device 1 for detecting the presence of moisture includes a detecting means including at least two electrically conductive moulded electrodes 2, 3 in a spaced apart arrangement. The spaced apart arrangement is to define an open circuit bridge. The electrodes 2,3 are made of any suitable durable and resilient and conductive material, and are preferably made of a conductive polymer. More preferably the electrodes 2,3 are formed of a un-plastisized conductive polyvinyl chloride ("PVC"), and including a filler of carbon black particles providing the conductive properties of the electrodes 2,3.

The electrodes preferably include raised or protruding conductive elements 4 aligned along each electrode 2,3. As seen in FIGS. 1 to 5, there are nine spaced apart protruding conductive elements 4 moulded along the length of each electrode 2,3. The electrodes 2,3 are advantageously aligned such that there are seen to be nine pairs of opposing conductive elements 4 with a predetermined distance or gap X between respective elements 4 in each electrode 2,3. The gap X can be any suitable distance and is substantially between about 2 to 5 millimeters in this embodiment. An advantage with this arrangement is that, when in use, moisture can be detected between any opposing pair of elements 4 and therefore the detector means can be considered to offer a detection device 1 that is relatively sensitive in detecting the presence of moisture.

Figure 3:
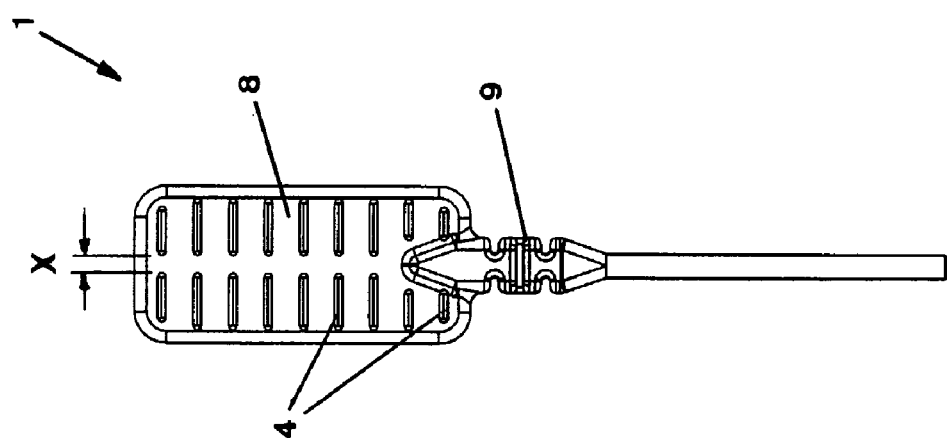
FIG. 3: Shows a side view of the overmoulded electrodes and cable of a device 1 in accordance with one preferred embodiment of the invention.
Figure 4:
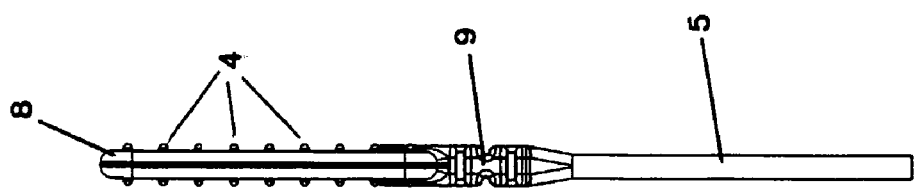
FIG. 4: Shows an end view of FIG. 3.

The electrodes 2,3 are adapted to allow wires 6,7 of an electrical cable 5 to be fastened or connected to respective electrodes 2,3. As seen in FIGS. 3 and 4, the electrodes 2, 3 are advantageously encased in a suitable durable and resilient and flexible non-conductive material 8, and in this embodiment of the invention they are preferably encased in a flexible non-conductive thermoplastics material 8. More desirably, the electrodes 2,3 are overmoulded in a non-conductive alloy type thermoplastic elastomer based on vulcanized silicone rubber particles in a thermoplastic matrix. One such example that can be applied to the device 1 is a thermoplastic silicone vulcanizate with a hardness of substantially about 50 shore A offering good tensile property retention and durability and hydrolytic resistance making such material particularly suitable in the device 1.

Figures 1, 2:
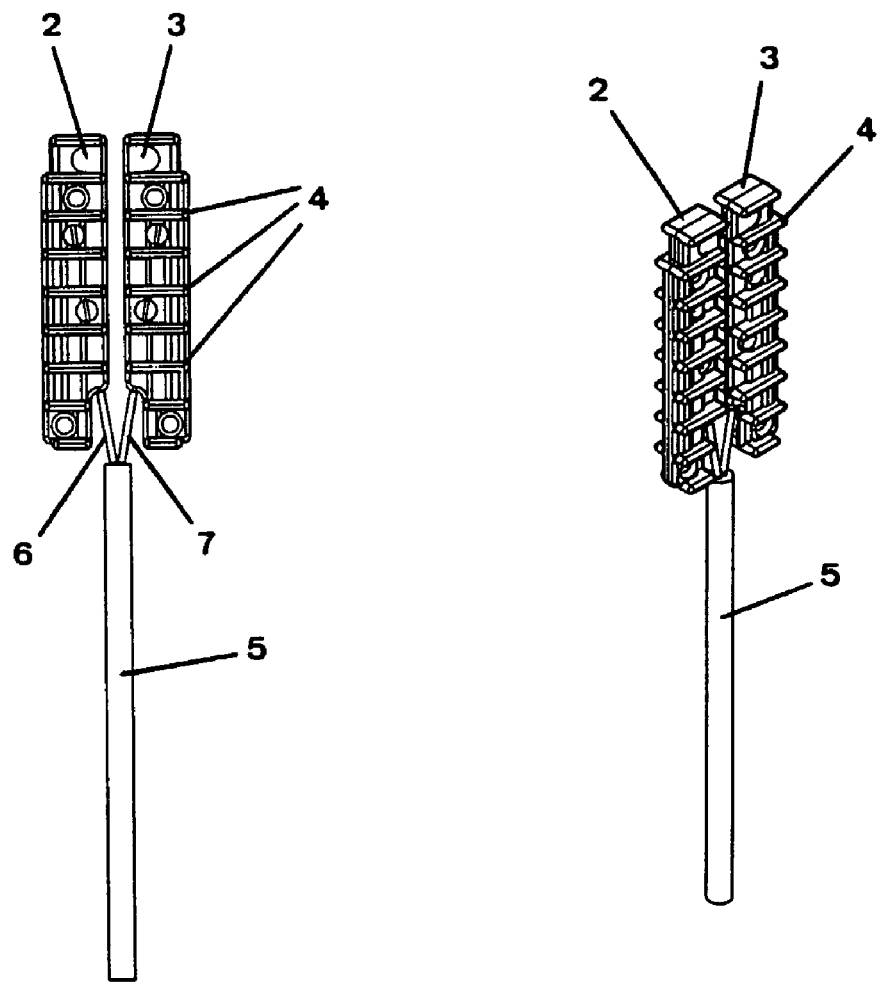
FIG. 1: Shows a side view of the electrodes and cable connected thereto before an overmoulding process.
FIG. 2: Shows a perspective view of FIG. 1.
Figure 5:
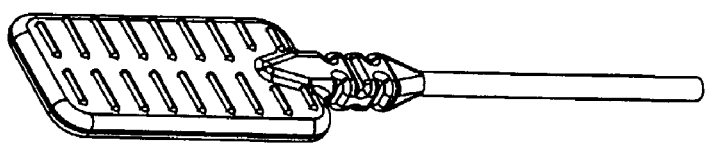
FIG. 5: Shows a perspective view of FIG. 3.

As seen in FIGS. 3 to 5, the non conductive overmoulded material 8 is advantageously shaped as an elongate paddle over the elongate electrodes 2,3 and forms a flexible and durable neck 9 at the base of the paddle. The neck 9 also moulds to the outer sheath of the cable 5.

The cable 5 in this non limiting embodiment is a two wire 6,7 stranded cable of 0.75 mm$^2$ with a PVC jacket. The length of the cable 5 in one non-limiting application is any suitable and desirable length required between the detector and the alarm means, and can be about 80 cm to a meter for many applications. The other end of the cable is terminated or connected to a plug adapted to insert into a suitable socket in the input to the signal processing means as detailed below.

As seen more clearly with reference to FIG. 4 showing an end view of the device 1, the end portions of the conductive elements 4, seen as conductive strips, protrude through the top surface of the overmoulded material 8. These protruding elements 4 are effectively the contact terminals of the electrical bridge between electrodes 2,3. The device 1 has been designed to offer substantial flexibility as the device 1 can be twisted and manipulated into position and can be flexed during operation without splitting or breaking the device 1. Further, as the overmoulding substantially encases the electrodes 2,3 and exposed wires 6,7 making it substantially water impervious, the device 1 can be repeatedly washed, even in hot water, and reused which is desirable for hygienic given its use in blood or urine drenched applications.

The paddle device 1 is seen to be relatively thin and flexible, and is about 40 millimeters long and 20 millimeters wide, and about 3.5 millimeters in thickness. The overall dimensions of the device 1 are to allow it to function well enough to detect moisture, and be small enough to be comfortable for use by a person. However, one of the main benefits of a soft and flexible paddle shaped detection device 1 is that it can be easily inserted into place and can provide a level of comfort for users.

Figure 6:
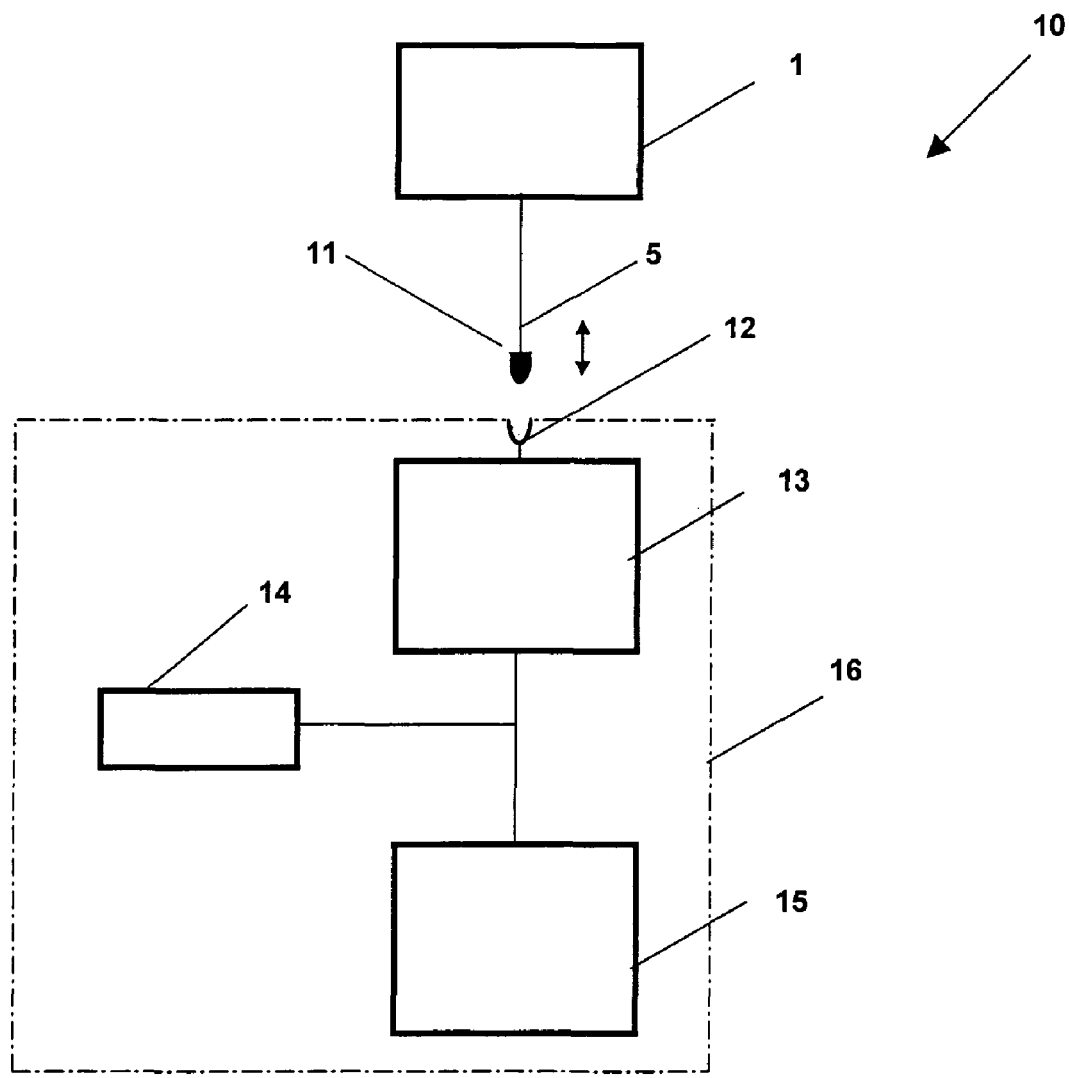
FIG. 6: Shows a schematic block diagram of main components of a moisture detecting apparatus 10 according to one preferred embodiment of the invention.
Figure 7:
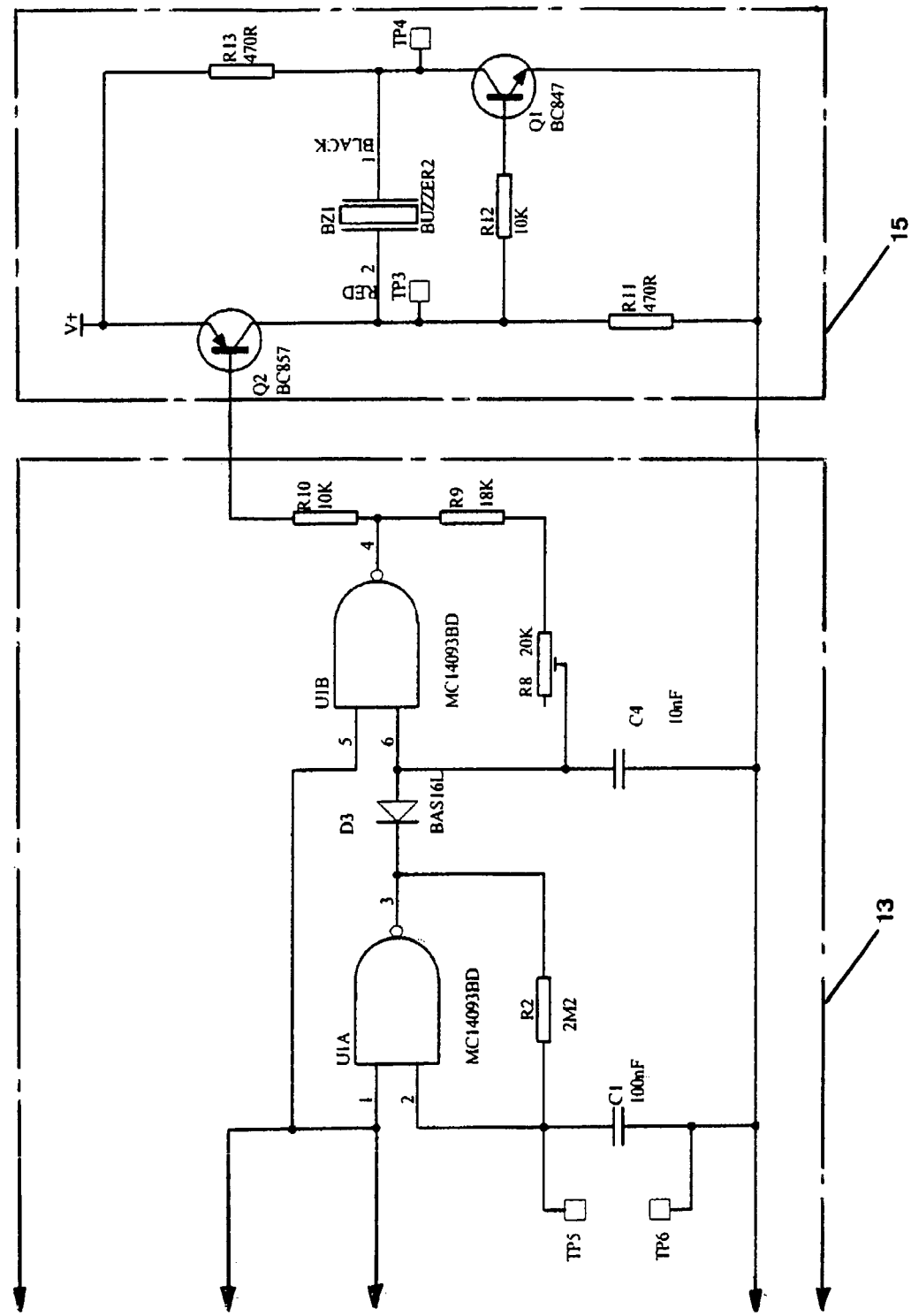
FIG. 7: Shows a circuit diagram of the moisture detecting apparatus 10.
Figure 7:
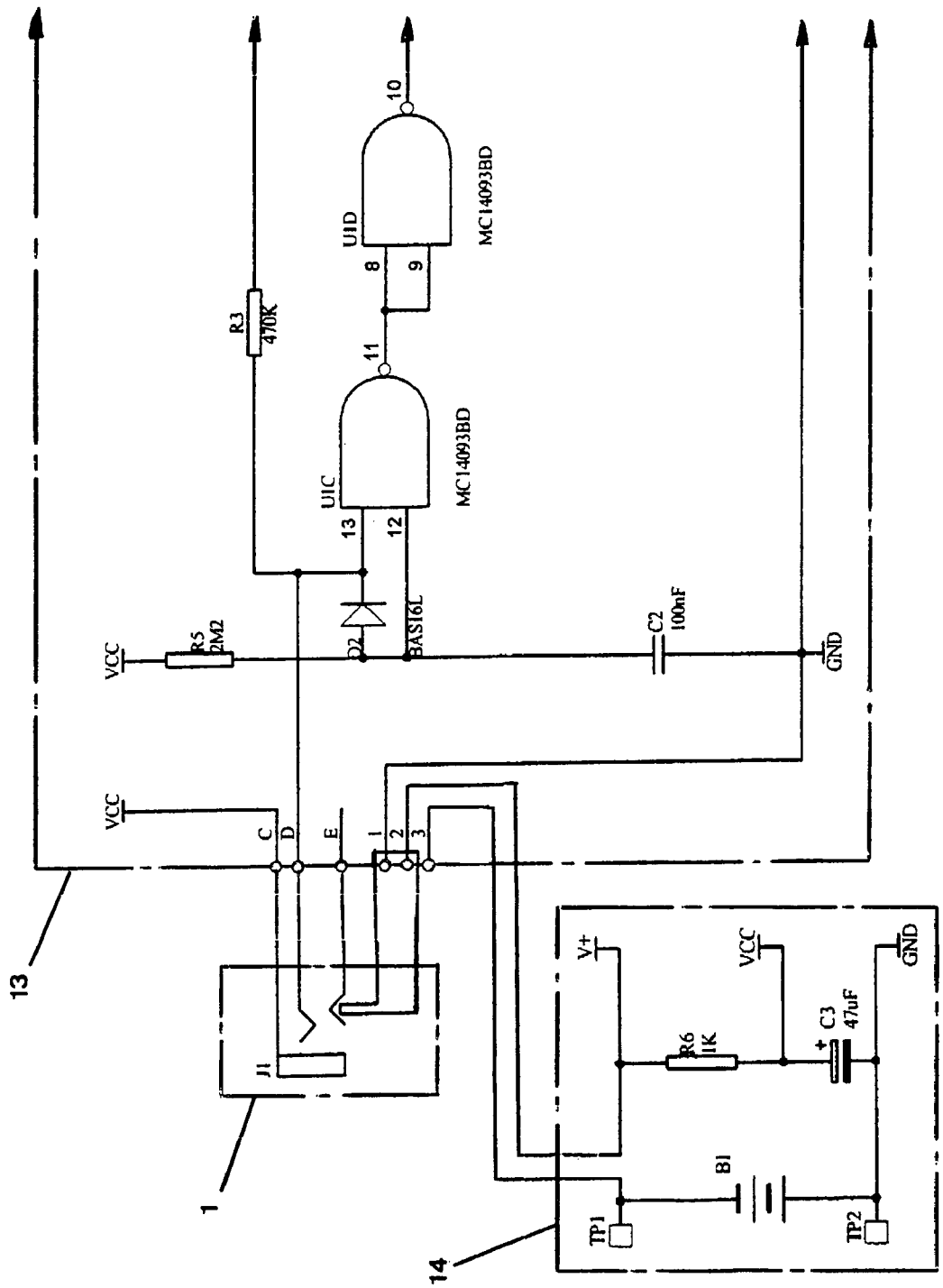

Referring now to FIGS. 6 and 7, schematic and circuit diagrams of a moisture detecting apparatus, generally referred to as 10, according to one preferred embodiment of the invention, is illustrated.

The moisture detection apparatus 10 of the invention, in one non-limiting application, is designed to assist an enuresis sufferer to develop an increased sensitivity to subliminal bladder contractions and ultimately may allow a user to learn to inhibit the reflex to pass urine, particularly when asleep.

The apparatus 10 preferably includes the moisture detection device 1 as described with reference to FIGS. 1 to 5. The cable 5 extending at one end of the device 1 is of any suitable and desirable length and can desirably include a plug connector 11 terminated at the other end of the cable 5. The plug 11 may be a mono plug, and the signal processing means 13 is adapted with a suitable connector or socket 12 for releasably receiving the plug 11 for operational purposes and for resetting the apparatus 10.

The apparatus 10 is broadly divided into main components as shown in FIG. 6. The sensing device 1 is electrically connected via the plug 11 to the socket 12 in a printed circuit board of the signal processing means 13. A power source means 14 preferably in the form of a battery comprising four button sized 1.5 volt cells supply about 6 volts direct current to the apparatus 10. The signal processing means 13 is configured and arranged with a plurality of suitable electrical circuit elements to monitor the output and state of the moisture detecting device 1 and to generate and process a signal suitable for feeding to the alarm indicator means 15. The alarm indicator means 15 may include any form of alert means including but not limited to an audible alarm and/or a visual display means such as, for example, a flashing light emitting diode or array of diodes (not shown) or other such indicator means to alert either a person using the apparatus 10 or a nurse or doctor or otherwise monitoring the person or patient.

The electrical circuit broadly represented as the signal processing means 13, the power source means 14 and the alarm indicator means 15 are desirably arranged in a compact and durable and resilient housing or casing 16. It is envisaged that the casing 16 will be as thin, lightweight and compact as possible to allow the circuitry to be protected and function effectively and also provide a level of comfort for users. The casing 16 can advantageously be of a size approximating about 50 millimeters in length and about 40 millimeters in width and about 15 millimeters in thickness.

In this embodiment an audible alarm means is used as the alert indicator means 15 and further details of the operation of the apparatus 10 is explained with reference to the circuit diagram illustrated in FIG. 7. It will be appreciated that this electrical circuit is supplied as one non-limiting example of the operation of the invention.

Referring now also to FIG. 7, the operation of the apparatus 10 is broadly noted as follows. To power up the apparatus 10, the plug 11 of the cable 5 is inserted into the socket 12 that is mounted to the PCB and electrically connected to the signal processing means 13. This action connects a 6 volt DC power from the power source means in the form of a battery circuit 14 to the signal processing means 13. The battery circuit 14 desirably includes a filter circuit with a capacitor C3 and a resistor R6 ensuring a smoother power supply to the main circuitry.

The device 1 is generally connected in an open circuit state such that it is dry across the outer surface 8 of the paddle with a high resistance between the conductive elements 4. The capacitor C2 ensures that the main circuit powers up in the correct state when power is supplied. The capacitor C2 will initially discharge to ensure that input PIN 12 of NAND gate U1C is at logic 0 which results in the output PIN 11 of gate U1C to be logic 1, and in turn the input to NAND gate U1D to be logic 0. Positive feedback through resistor R3 further keeps the circuit in this state. Capacitor C2 will be charged through resistor R5 such that PIN 12 of gate U1C will be at logic 1.

The device 1 is connected through the cable 5 to the resistor R3 to form a potential divider, and a variable voltage depending on the relative resistance at PIN 13 of gate U1C. When the conductive elements 4 are bridged by moisture, the resistance drops across the elements 4 and electrodes 2,3 such that the voltage will rise across PIN 13 of gate U1C and cross the threshold of gate U1C. At this instant, both inputs to gate U1C with PIN 12 and PIN 13 will be at logic 1 and the output of gate U1C will change to logic 0 resulting in both inputs to gate U1D being at logic 0 resulting in the output of gate U1D changing to logic 1 and positive feedback through resistor R3 will ensure this state remains the same until reset.

The present invention offers the additional feature of effectively isolating the electrodes 2, 3 of the device 1 once moisture has been detected and the main circuit has been triggered. This is achieved in this circuit by the fact that once the output of gate U1D changes to logic 1 and positive feedback through resistor R3 ensure this state remains the same, the voltage drop across the electrodes 2, 3 is reduced to 0 volts. Because the voltage across the electrodes 2, 3 and the resistor R3 are at the same voltage, there can not be any current flow across the electrodes 2, 3 and therefore effectively the device 1 is isolated. This effect is desirable in applications whereby the device 1 is being used to detect urine as electrical current can cause urine to become acidic through electrolysis, with a risk of skin irritation.

As the output of gate U1D has changed to logic 1, the alarm means in the form of a piezoelectric ceramic speaker BZ1 is actuated and starts beeping to alert a user to the presence of moisture. It is seen that integrated circuit U1B generates a high frequency tone at about 3.7 kHz that is modulated on/off by operation of modulator U1A and diode D3 at a rate of about 4 Hz. The modulation frequency is set by operation of capacitor C1 and resistor R2. The frequency of the speaker BZ1 is set by operation of capacitor C4 and resistors R8 and R9 and whereby the frequency and hence the volume of the speaker BZ1 can be tuned by adjusting R8 for the desired output.

Optionally if a continuous tone is required rather than an intermittent or beeping tone the on/off modulation effect can be disabled by bridging or connecting across pins TP5 and TP6 to short out capacitor C1.

It is seen that the output of the signal processing means 13 is buffered by the alarm indicator means 15 by operation of transistors Q1 and Q2 before driving the speaker BZ1. A bridge circuit is formed by operation of the circuit elements Q1, Q2, R11 and R13 resulting in a drive signal fed to the speaker BZ1 that is almost double the supply voltage of 6 volts.

It is seen that the speaker BZ1 will continue to emit a tone until the cable 5 is unplugged from the socket 12 which causes the circuit to be turned off.

The apparatus 10 is considered to be particularly suitable for use by enuresis sufferers. As the casing 16 is quite compact, it can adapted to be attached to a user's clothing by any suitable fastening means. In the case of problems with enuresis sufferers who are sleeping, suitable attachment means for attaching the casing 16 housing the main circuitry can be provided so that the casing unit 16 is attached close to the head of the wearer.

In one application of the apparatus 10 for an enuresis sufferer, the casing 16 part of the apparatus 10 can be attached to the shoulder or associated clothing of a wearer such that the alarm indicator means 15 is mounted close to the wearer's head. The cable 5 can be plugged into the socket 12 and the device 1 can then be positioned inside his or her pants in a suitable position to detect the presence of urine when the user passes urine. It is seen then that when urine closes the electrical bridge between at least any one respective pair of elements 4 between electrodes 2,3 the alarm indicator means 15 will be is activated and the sleeping person should wake up and be made conscious of the fact that they are passing urine. It is seen then that the alarm advantageously functions as a stimulus to assist in bladder training by the person wearing the apparatus 10 of the invention. Once activated the user may remove the plug 11 from the socket 12 and later reinsert the plug 11 to reset the apparatus 10.

It is further considered that the apparatus 10 of the invention may also be useful for applications such as the detection of blood leaking around the site of insertion of a needle during dialysis, particularly during nocturnal dialysis. Further, high levels of perspiration may be detected for persons suffering hypoglycaemia in insulin dependent diabetics.

Figure 8:
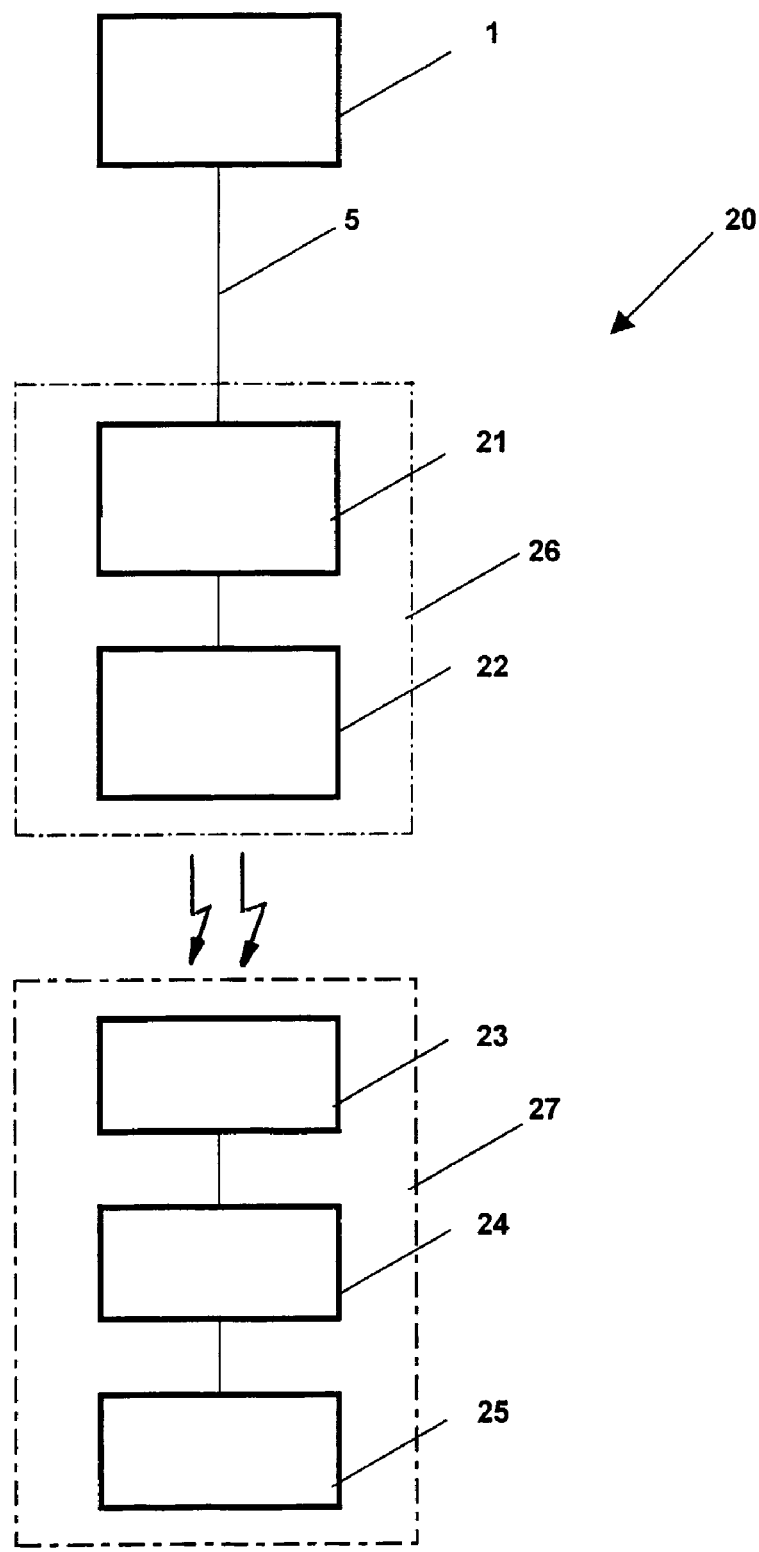
FIG. 8: Shows a schematic block diagram of main components of a moisture detecting apparatus 20 according to a second preferred embodiment of the invention.

Referring now to FIG. 8, a schematic block diagram of main components of a moisture detecting apparatus 20, according to a second preferred embodiment of the invention, is illustrated. In this embodiment the device 1 is close to the signal processing means and the alarm means can be placed remote from the device 1 by a user or by another person reasonably close that is monitoring the person wearing the sensing device 1.

In this apparatus 20, the cable 5 from the moisture sensing device 1 is connected to terminals of a signal processing means 21. The signal processing means 21 also includes a transmitter 22. The transmitter 22, once activated when the signal processing means detects and processes a positive signal from the device 1, transmits a suitable signal to a receiver means 23 that is fed to a control means 24 that is adapted to trigger an alarm indicator means 25. Many aspects and principles of this electrical circuit and associated elements can be similar to the apparatus 10 as already described and will not be repeated.

One method of operation is broadly described as follows. The signal processing means 21 is configured and arranged to monitor the resistance across the electrodes 2, 3 of the device 1. A suitable power supply means in the form of a battery is provided along with a suitable on/off switch. When the resistance drops below a predetermined threshold level because urine has formed a conductive path across elements 4 between electrodes 2,3, the output of an integrated circuit formed as a Schmitt trigger changes state such that its output changes to logic 0 and this change of state is sensed by an input to a second integrated circuit (IC), such as, for example, an Atmel AT86RF401 IC functioning as a signal processor and radio frequency microtransmitter operating in a band of between about 300 to 450 MHz. When the second IC receives a signal indicating that moisture on the device 1 is present, it starts transmitting at about 750 bps at a low power level of about 1 milliwatt at a frequency of say about 315.788 MHz. The antenna that is used may be a loop antenna that set in place around the outside of a printed circuit board to which components of the signal processing means 21 and related elements are mounted.

The transmitting signal may be encoded if required, and data that is transmitted may be a 32 bit number unique to the transmitter. The transmitter repeatedly transmits the data to be received by an associated receiver means 23 that is monitoring for transmission of the unique 32 bit number.

The receiver means 23 is also desirably battery powered and includes a suitable radio frequency receiver (for example a Micrel MICRF009BM IC) and associated circuit elements and RF antenna, signal processing means including a microprocessor controller unit (for example an ATMEL ATTINY12 IC) referred to as a control unit 24, with associated circuit elements, and a suitable alarm indicator means 25.

The receiver circuitry can be configured to constantly monitor for the particular 32 bit data that may be transmitted from the transmitter means 22. If the transmitter means 22 is transmitting the 32 bit data once activated by the device 1, the receiver means 23 will receive the signal and feed the signal to the microprocessor control unit 24. The control unit 24 then pulses an oscillator circuit that drives the alarm indicator means 25 in the form of a buzzer or piezo-electric speaker.

The circuitry at the transmitting side is housed in a suitable compact casing 26. The circuitry at the receiving side is also housed in a suitable compact casing 27.

It is considered that the alarm means 25 can be conveniently positioned anywhere within the signal receiving range of transmission, and as such can be either close to the user or be remotely monitored by a caregiver or nurse or other person monitoring the user.

Wherein the aforegoing reference has been made to integers or components having known equivalents, then such equivalents are herein incorporated as if individually set forth. Accordingly, it will be appreciated that changes may be made to the above described embodiments of the invention without departing from the principles taught herein.

It is to be understood that the above description is intended to be illustrative, and not restrictive. Additional advantages of the present invention will become apparent for those skilled in the art after considering the principles in particular form as discussed and illustrated. Thus, it will be understood that the invention is not limited to the particular embodiments described or illustrated, but is intended to cover all alterations or modifications which are within the scope of the appended claims.

The invention claimed is:

1. A device for detecting the presence of moisture, the device including a detector means including at least two spaced apart electrodes defining an open electrical bridge and each electrode being electrically connectable to a signal generating means via a wire, the electrodes being configured and arranged, in use, to provide a path for electricity to conduct across a predetermined distance or gap between the electrodes when a sufficient amount of moisture bridges the distance or gap between the electrodes, and wherein the conductive electrodes are overmoulded and encased in a flexible non-conductive and water impervious material with each said conductive electrode including at least one protruding exposed conductive element extending beyond the outer surface of the non-conductive material and being separated by the predetermined distance or gap between the respective conductive elements, and wherein the overmoulded non-conductive material bonds with the conductive elements so as to prevent the absorption or ingress of moisture into the device, wherein the conductive electrodes are made of a flexible conductive plastics material that are overmoulded with a suitable flexible non-conductive plastics material, and wherein the conductive plastics material only protrudes through the overmoulded non-conductive plastics material enough to form the exposed conductive elements, and including a signal processing means configured and arranged to detect a change of state across the electrodes and actuate an alarm means, the signal processing means including an arrangement of circuit elements configured and arranged, in use, to prevent current from flowing through the detecting device once the alarm means is activated, including a means for monitoring the state of the electrical bridge of the moisture detecting device to determine whether the state of the bridge is electrically open or closed, a means for generating and processing an alarm signal when the electrical bridge is closed across the electrodes, and a means for isolating the electrical bridge between the electrodes upon detection of a closed electrical bridge.

2. A device according to claim 1, wherein the plastics material is a flexible thermoplastic silicone vulcanizate material.

3. A device according to claim 1, wherein each said conductive electrode includes nine protruding conductive elements separated by the predetermined distance or gap between the electrodes.

4. A device according to claim 1, wherein a pair of conductive electrodes are configured and arranged with nine protruding conductive elements formed in each said electrode, the conductive elements being exposed through the overmoulded non-conductive plastics material, and wherein the nine opposing conductive elements are aligned along the length of the detector means with the predetermined distance or gap between each opposing pair of said conductive elements.

5. A device according to claim 1, wherein the wire is adapted to be releasably connectable to the signal processing means.

6. A moisture detection apparatus including a moisture detecting device including at least two spaced apart electrodes defining an open electrical bridge and each electrode being electrically connectable to a signal generating means via a wire, the electrodes being configured and arranged, in use, to provide a path for electricity to conduct across a predetermined distance or gap between the electrodes when a sufficient amount of bodily fluid or moisture on the body of a person bridges the distance or gap between the electrodes, and wherein the conductive electrodes are made of a conductive plastics material that are overmoulded and encased in a non-conductive and water impervious plastics material with each said conductive electrode including at least one protruding exposed conductive element extending beyond the outer surface of the non-conductive material and being separated by the predetermined distance or gap between the respective conductive elements, and wherein the overmoulded non-conductive material bonds with the conductive elements so as to prevent the absorption or ingress of bodily fluid or moisture from the body of the person into the device, and wherein the apparatus includes a signal processing means configured and arranged to detect a change of state across the electrodes and actuate an alarm means, and a power source means for powering the signal processing means and the alarm means, the signal processing means including an arrangement of circuit elements configured and arranged, in use, to prevent current from flowing through the detecting device once the alarm means is activated, including a means for monitoring the state of the electrical bridge of the moisture detecting device to determine whether the state of the bridge is electrically open or closed, a means for generating and processing an alarm signal when the electrical bridge is closed across the electrodes, and a means for isolating the electrical bridge between the electrodes upon detection of a closed electrical bridge.

7. An apparatus according to claim 6, wherein the signal processing means and the alarm means are configured and arranged within a housing, and wherein the detector means is located remotely from the housing and connected via the wire to a removably attachable connector means to the input of the signal processing means.

8. An apparatus according to claim 6, wherein the signal processing means includes an arrangement of circuit elements configured and arranged, in use, to generate a suitable input alarm signal to an audible alarm means so as to actuate an audible alarm in response to the detection of bodily fluid or moisture by the detector means, including a means for monitoring the state of the electrical bridge of the moisture detecting device to determine whether the state of the bridge is electrically open or closed, and a means for generating and processing the input alarm signal when the electrical bridge is closed across the electrodes and feeding the alarm signal to the audible alarm.

9. A device according to claim 6, wherein the alarm is a piezoelectric ceramic speaker.

10. An apparatus according to claim 6, wherein the signal processing means includes a transmitter means that receives a suitable input signal and transmits an output signal to a receiver means, and wherein the receiver means receiving a signal from the transmitter means to actuate an audible alarm means in response to the detection of bodily fluid or moisture by the detector means.

11. An apparatus according to claim 6, wherein the power source means is a battery supplying a direct current voltage supply.

12. A device according to claim 6, wherein the bodily fluid or moisture being detected includes [bodily fluid such as] urine and/or blood and/or excessive perspiration.

13. A device according to claim 6, wherein the signal processing means is provided with an electrode isolating means configured to prevent electrolysis when the moisture being detected is in the form of bodily fluid.

14. An apparatus according to claim 6, wherein the signal processing means and the alarm means are configured and arranged within a housing, and wherein the detector means is located remotely from the housing and connected via the wire to a removably attachable connector means to the input of the signal processing means.

15. An apparatus according to claim 6, wherein the signal processing means includes an arrangement of circuit elements configured and arranged, in use, to generate a suitable input alarm signal to an audible alarm means so as to actuate an audible alarm in response to the detection of bodily fluid or moisture by the detector means, including a means for monitoring the state of the electrical bridge of the moisture detecting device to determine whether the state of the bridge is electrically open or closed, and a means for generating and processing the input alarm signal when the electrical bridge is closed across the electrodes and feeding the alarm signal to the audible alarm.

16. An apparatus according to claim 6 wherein a pair of conductive electrodes are configured and arranged with nine protruding conductive elements formed in each said electrode, the conductive elements being exposed through the overmoulded non-conductive plastics material, and wherein the nine opposing conductive elements are aligned along the length of the detector means with the predetermined distance or gap between each opposing pair of said conductive elements.

17. A device according to claim 6, wherein the plastics material is a flexible thermoplastic silicone vulcanizate material.

18. A device according to claim 6, wherein each said conductive electrode includes nine protruding conductive elements separated by the predetermined distance or gap between the electrodes.

19. A device according to claim 6, wherein a pair of conductive electrodes are configured and arranged with nine protruding conductive elements formed in each said electrode, the conductive elements being exposed through the overmoulded non-conductive plastics material, and wherein the nine opposing conductive elements are aligned along the length of the detector means with the predetermined distance or gap between each opposing pair of said conductive elements.

20. A device according to claim 6, wherein the wire is adapted to be releasably connectable to the signal processing means.

* * * * *